(12) United States Patent
Stolovitzky et al.

(10) Patent No.: US 10,612,084 B2
(45) Date of Patent: Apr. 7, 2020

(54) REDUCTION OF ENTROPIC BARRIER OF POLYELECTROLYTE MOLECULES IN A NANOPORE DEVICE WITH AGAROSE GEL

(71) Applicant: International Business Machines Corporation, Armonk, NY (US)

(72) Inventors: Gustavo A. Stolovitzky, Riverdale, NY (US); George F. Walker, New York, NY (US); Chao Wang, Ossining, NY (US); Deqiang Wang, Ossining, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 403 days.

(21) Appl. No.: 14/585,236

(22) Filed: Dec. 30, 2014

(65) Prior Publication Data

US 2015/0285764 A1 Oct. 8, 2015

Related U.S. Application Data

(60) Provisional application No. 61/976,562, filed on Apr. 8, 2014.

(51) Int. Cl.
| | |
|---|---|
| *C12Q 1/6869* | (2018.01) |
| *C12N 15/10* | (2006.01) |
| *G01N 27/447* | (2006.01) |

(52) U.S. Cl.
CPC ......... *C12Q 1/6869* (2013.01); *C12N 15/101* (2013.01); *G01N 27/44747* (2013.01); *G01N 27/44791* (2013.01)

(58) Field of Classification Search
CPC ................ C12Q 1/6869; C12N 15/101; C12N 15/1003; C12N 15/1006; C12N 15/1017; G01N 27/44747; G01N 27/44773; G01N 27/447; G01N 27/44717; G01N 27/44778; G01N 27/44791
See application file for complete search history.

(56) References Cited

U.S. PATENT DOCUMENTS

| | | |
|---|---|---|
| 8,003,319 B2 | 8/2011 | Polonsky et al. |
| 2006/0210995 A1 | 9/2006 | Joyce |

(Continued)

OTHER PUBLICATIONS

Gustavo A. Stolovitzky, et al.; "Reduction on Entropic Barrier of Poyelectrolyte Molecules in a Nanopore Device With Agarose Gel"; U.S. Appl. No. 14/747,017, filed Jun. 23, 2015.
List of IBM Patents or Patent Applications Treated As Related—Date Filed: Aug. 31, 2015; 1 page.
G. Ando, et al., "Directly Observing the Motion of DNA Molecules new Solid-State Nanopores," ACS Nano, vol. 6., No. 11., 2012, pp. 10090-10097.

(Continued)

*Primary Examiner* — Daniel P Malley, Jr.
(74) *Attorney, Agent, or Firm* — Cantor Colburn LLP; Vazken Alexanian

(57) ABSTRACT

A mechanism is provided for reducing entropy of a polyelectrolyte before the polyelectrolyte moves through a nanopore. A free-standing membrane has the nanopore formed through the membrane. An agarose gel is formed onto either and/or both sides of the nanopore in the membrane. The agarose gel is a porous material. The polyelectrolyte is uncoiled by driving the polyelectrolyte through the porous material of the agarose gel via an electric field. Driving the polyelectrolyte, having been uncoiled and linearized by the agarose gel, into the nanopore is for sequencing.

12 Claims, 11 Drawing Sheets

(56) References Cited

U.S. PATENT DOCUMENTS

| | | | |
|---|---|---|---|
| 2009/0221443 A1* | 9/2009 | Heller | B82Y 30/00 506/16 |
| 2010/0035260 A1 | 2/2010 | Olasagasti et al. | |
| 2011/0036994 A1* | 2/2011 | Frayling | G01N 21/648 250/459.1 |
| 2012/0040343 A1 | 2/2012 | Timp et al. | |
| 2012/0193236 A1* | 8/2012 | Peng | G01N 33/48721 204/603 |
| 2013/0062206 A1* | 3/2013 | Afzali-Ardakani | C25D 5/028 204/479 |
| 2013/0161194 A1 | 6/2013 | Jeon et al. | |
| 2014/0299473 A1 | 10/2014 | Walker | |
| 2014/0299474 A1* | 10/2014 | Walker | G01N 27/44747 204/470 |

OTHER PUBLICATIONS

G. Walker, et al., "Controlled Translocation of Macromolecules Employing a Funnel Nanopore Structure and a Gel," U.S. Appl. No. 13/856,550, filed Apr. 4, 2013; 32 pages.

J. Mannion, et al., "Conformational Analysis of Single DNA Molecules Undergoing Entropically Induced Motion in Nanochannels," Biophysical Journal, vol. 90., No. 12, 2006, pp. 4538-4545.

J. Narayanan, et al., "Determination of Agarose Gel Pore Size: Absorbance Measurements Vis a Vis Other Techniques," Journal of Physics: Conference Series, vol. 28., No. 1 2006, pp. 83-86.

M. Wanunu, et al., "Electrostatic Focusing of Unlabelled DNA into Nanoscale Pores Using a Salt Gradient," Nature Nanotechnology, vol. 5., No. 2, 2009, pp. 160-165.

* cited by examiner

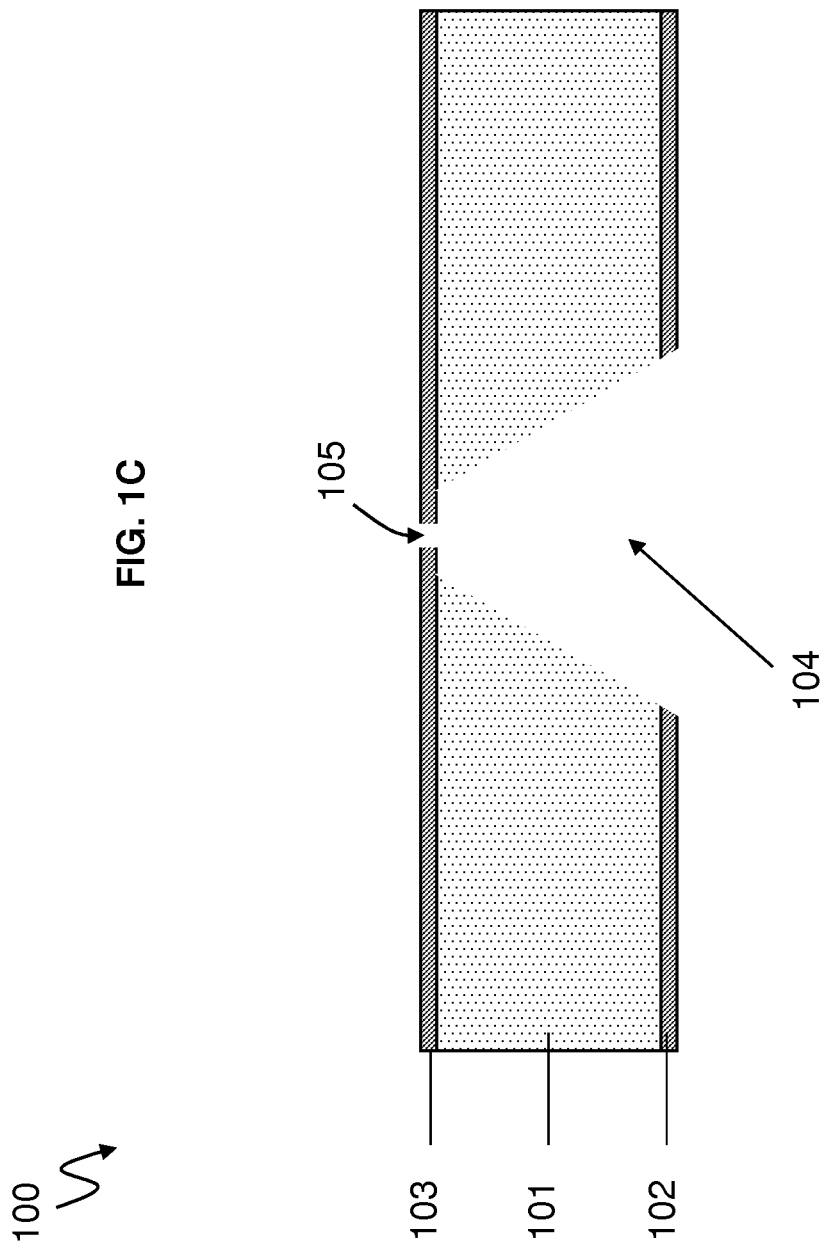

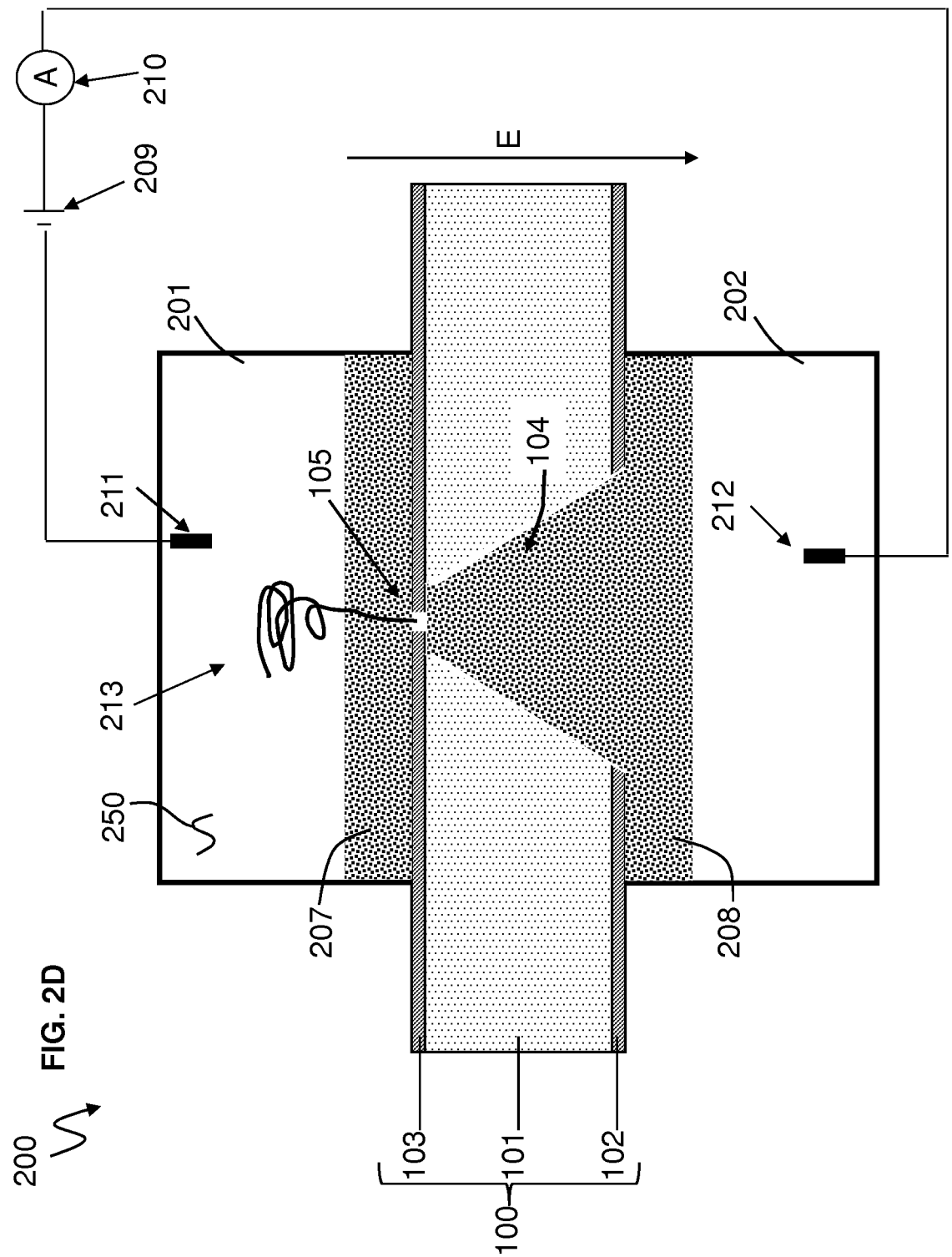

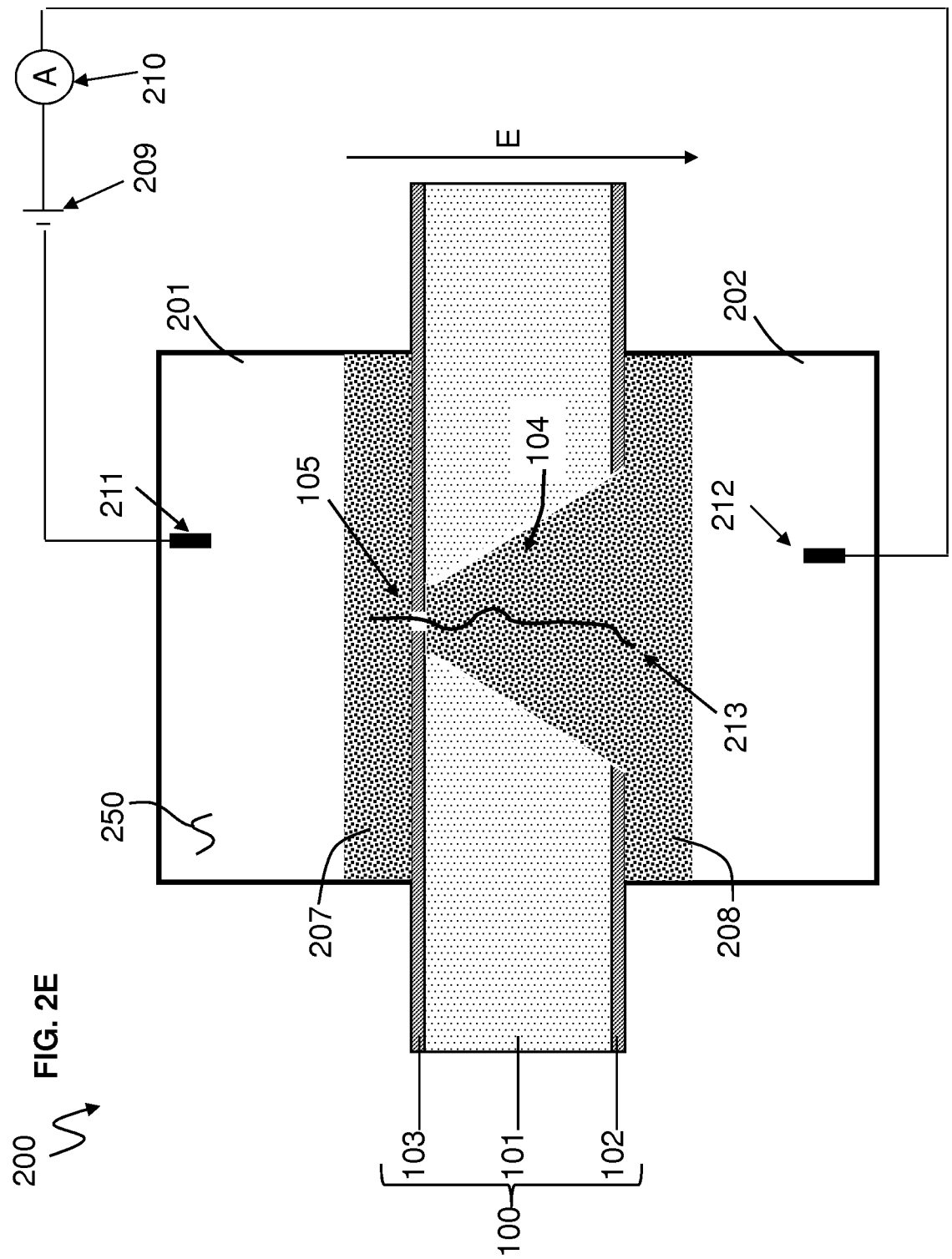

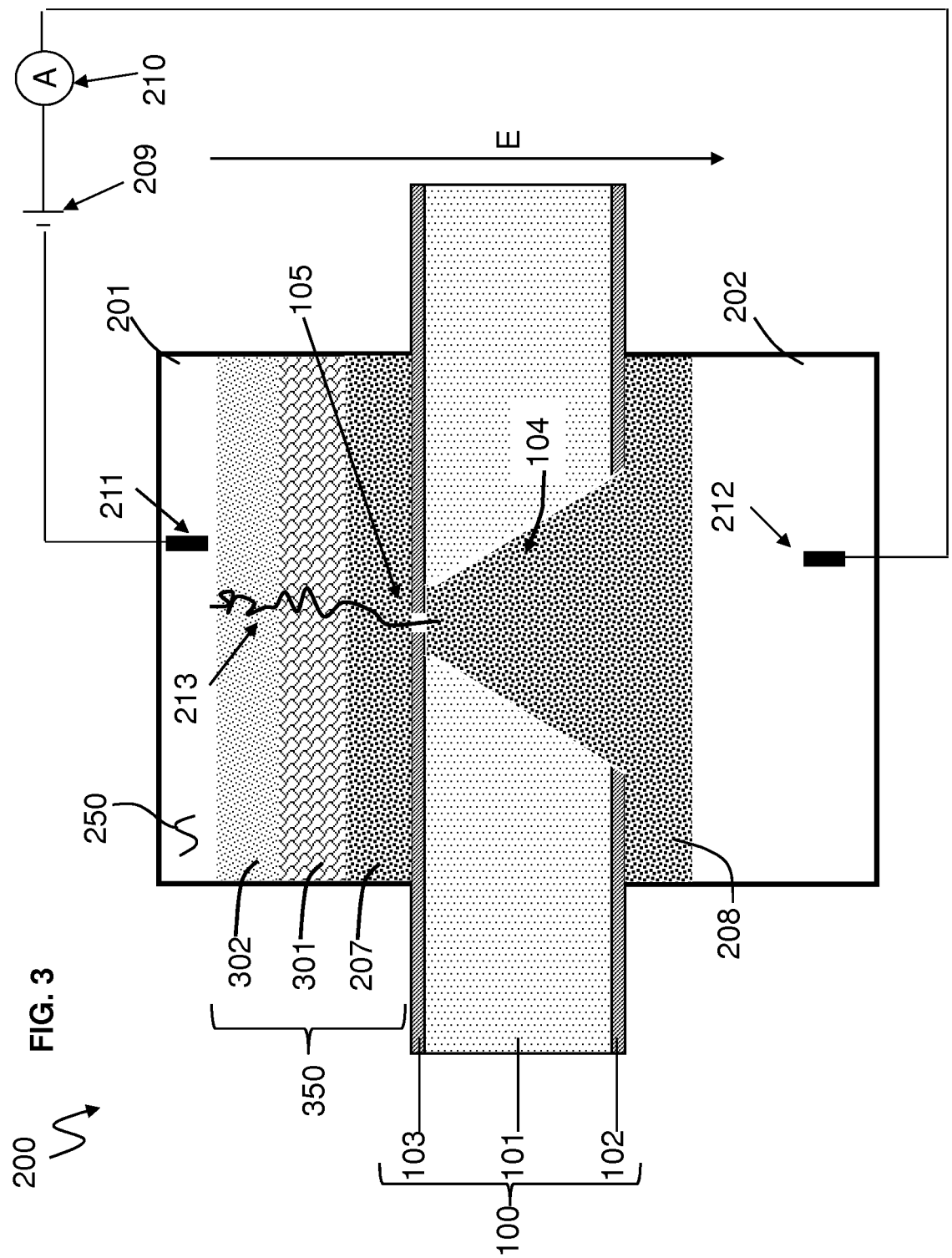

REDUCTION OF ENTROPIC BARRIER OF POLYELECTROLYTE MOLECULES IN A NANOPORE DEVICE WITH AGAROSE GEL

DOMESTIC PRIORITY

This application claims priority to Provisional Application No. 61/976,562, filed on Apr. 8, 2014, which is herein incorporated by reference in its entirety.

BACKGROUND

The present invention relates to nanopore/nanochannel devices, and more specifically, to reducing the entropy of molecules via agarose gel in nanopore/nanochannel devices.

Nanopore sequencing is a method for determining the order in which nucleotides occur on a strand of deoxyribonucleic acid (DNA). A nanopore (also referred to a pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to an embodiment, a method for reducing entropy of a polyelectrolyte before the polyelectrolyte moves through a nanopore is provided. The method includes providing a free-standing membrane having the nanopore formed through the membrane, and forming an agarose gel onto at least one of either or both sides of the nanopore in the membrane. The agarose gel is a porous material. The method include uncoiling the polyelectrolyte by driving the polyelectrolyte through the porous material of the agarose gel via an electric field, and driving the polyelectrolyte, having been uncoiled and linearized by the agarose gel, into the nanopore for sequencing.

According to an embodiment, a system for reducing entropy of a polyelectrolyte before the polyelectrolyte moves through a nanopore is provided. The system includes a free-standing membrane having the nanopore formed through the membrane, a top fluidic reservoir on one side of the membrane and a bottom fluidic reservoir on an opposing side of the membrane, and an agarose gel formed onto at least one of either or both sides of the nanopore in the membrane. The agarose gel is a porous material. An electric field generated by a voltage source drives the polyelectrolyte through the porous material of the agarose gel to uncoil the polyelectrolyte. Driving the polyelectrolyte, having been uncoiled and linearized by the agarose gel, into the nanopore is for sequencing.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 1C illustrates forming the nanometer pore in the membrane according to an embodiment

FIG. 2D illustrates that the polyelectrolyte is linearized and uncoiled by passing through the agarose before entering into the nanopore according to an embodiment.

FIG. 2E illustrates the full length of the linearized and uncoiled polyelectrolyte within the agarose gel and through the nanopore according to an embodiment.

FIG. 3 illustrates multilayers (gradient) of agarose gels with different concentrations corresponding to different pore sizes according to an embodiment.

DETAILED DESCRIPTION

Figure 1A:
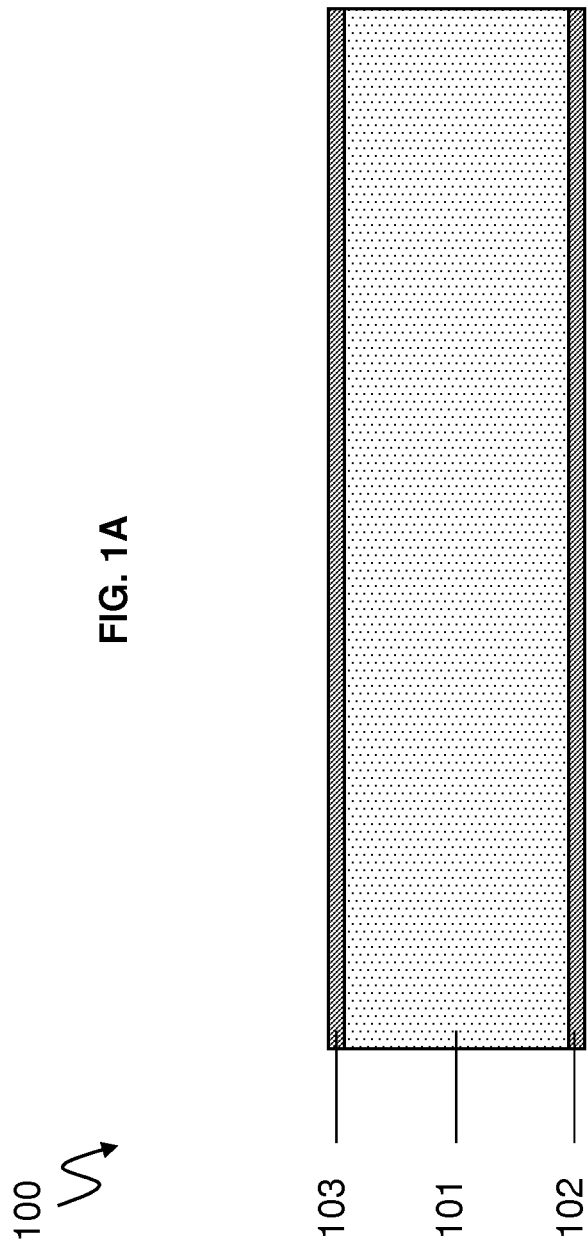
FIG. 1A a process flow to fabricate a free-standing membrane with a nanometer pore according to an embodiment.

Embodiments provide a method and nanopore device to reduce the entropic barrier to nanopores with agarose gel for polyelectrolyte sensing, such as DNA or RNA sequencing.

The nanopore device (which has holes with a few nanometers in diameter) is a promising technology for next-generation DNA sequencing. It consists of a planar substrate with a thin insulating membrane (typically tens of nanometers thick) with a nanometer-sized pore drilled through. When the polyelectrolyte (DNA, RNA, peptide, etc.) is loaded in the conductive liquid on both sides of the membrane, the polyelectrolyte is forced by an external field to translocate through the nanopore opening. Hence, electrical signals can be recorded to detect the molecules, nucleotides and/or bases of the polyelectrolyte.

To make the nanopore devices reliable for fast sequencing, several criteria may need to be satisfied. First, the polyelectrolyte needs to be linearized, rather than coiled, in the nanopore for reliable sequential reading. Second, for uniform motion control of polyelectrolytes which are longer than the membrane thickness, the electric field (E) needs to be applied uniformly across the whole membrane and extend into the conductive liquid. Third, a pre-stretching of the polyelectrolyte before its entry into the nanopore is required for fast translocation without clogging the nanopore.

However, the above challenges may still remain unresolved in conventional nanopore devices that rely only on a thin and single-layer membrane (biological or artificial) and pose very large entropic barriers to long polyelectrolyte molecules. In the bulk liquid solution of such devices, where there is no geometrical confinement, the long polyelectrolyte molecules stay in a coiled state and their entropy is the largest in this coiled state; in contrast, within the nanopore region, the polyelectrolyte molecules experience great confinement and force themselves to decoil into a linear state, corresponding to very small entropy.

Such a huge entropy difference (between the coiled and uncoiled states for the polyelectrolyte) causes a significantly high energy barrier for the long polyelectrolyte to overcome and hence translocate, and the huge entropy difference greatly lowers the translocation speed of the polyelectrolyte through the nanopore. Furthermore, an abrupt electric field change over a very small distance at the nanopore entrance vicinity can drive in the coiled polyelectrolyte into the confined nanopore, and thus cause very long clogging events. Additionally, such a large entropy change can cause configurational instabilities of the polyelectrolyte molecules and even drive the polyelectrolyte to coil and decoil (i.e., uncoil) inside the nanopore. All the above issues can lead to reduced and clogged events and thus severely affect the proper detection of bases and/or nucleotides.

Conventionally, different methods are used to enhance the translocations of DNA for nanopores, like salt gradient and high voltages. Those methods only change the electrical field distribution close to the nanopores entry. Salt gradient structures were used to uncoil the DNA before it moved through nanochannels, because those micro-structures can help to reduce the entropy barrier to nanochannels. However, such micro/nano-patterned structures are very difficult to integrate into the vicinities of the nanopore openings.

Embodiments provide effective methods that utilize agarose gels to improve the electric field uniformity and also lower the entropic barrier, all of which helps the polyelectrolyte to move through nanopore in a linearized (straight) state.

Embodiments have various benefits by utilizing the agarose gel as discussed herein: (1) the agarose gel provides millimeter-scale nanoconfinement to the polyelectrolyte molecules and pre-stretch them before their entry into the nanopores, hence greatly lowering the entropic barrier; (2) the agarose gel also greatly reduces the bulk conductivity and extends the electric fields much longer than (i.e., uniformly beyond) the membrane itself, which is beneficial to higher molecular capture rate and higher translocation events; and (3) the agarose gel has different porous structures at different concentrations of agarose, and thus provides easy tuning of the polyelectrolyte confinement and electric field distribution.

Embodiments integrate agarose gel and the nanopore device together for DNA sequencing. The agarose gel uncoils the DNA before reaching the entry of the nanopore. Then, the nanopore reads the single base information when the single-stranded DNA passes through nanopore. The method helps the DNA move through nanopore by reducing the entropic barrier to nanopore entry.

Figure 1B:
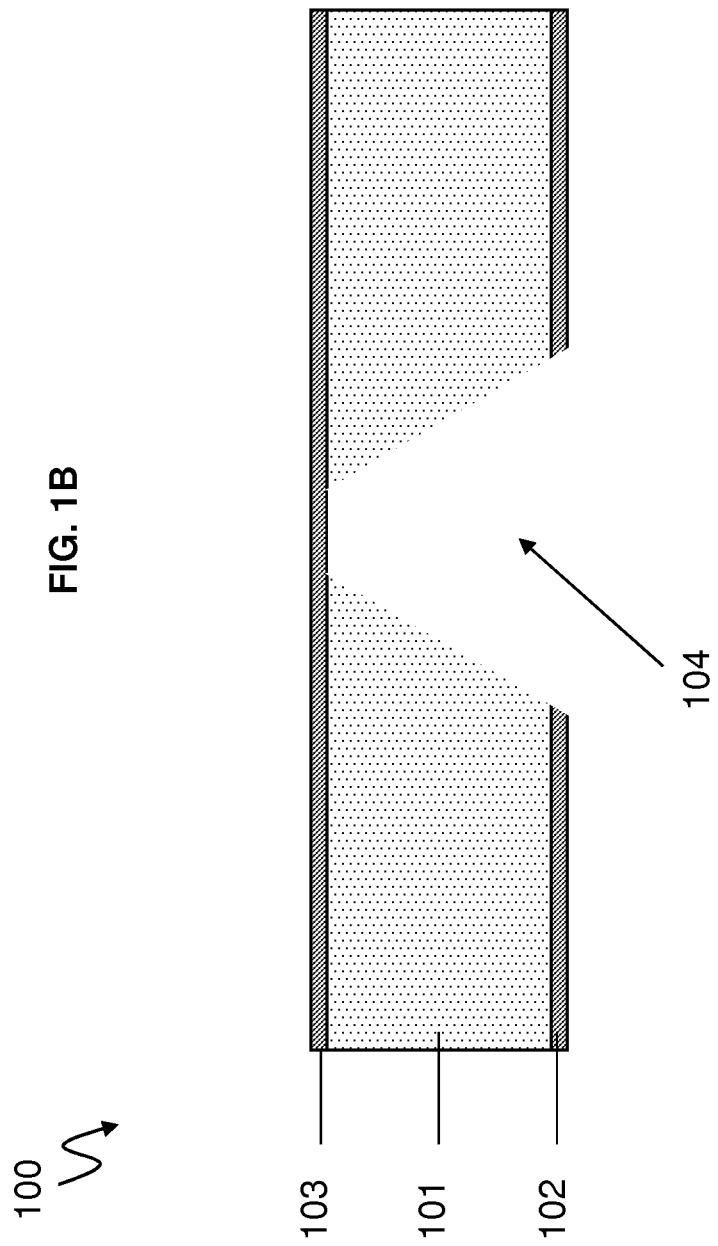
FIG. 1B illustrates forming a cavity in the backside of the membrane according to an embodiment.

Now turning to the figures, FIGS. 1A, 1B, and 1C (generally referred to as FIG. 1) illustrate the process flow to fabricate a membrane 100 with a single nanometer pore (i.e., nanopore) according to an embodiment. FIG. 1 shows a cross-sectional view of the membrane 100 which is a nanopore device.

In FIG. 1A, substrate 101 is any electrically insulating substrate (such as silicon formulated to be electrically insulating). Insulating layers 102 and 103 are respectively deposited on the bottom and top of the substrate 101. The insulating layers 102 and 103 are electrically insulating films, such as silicon nitride, silicon dioxide, etc. The insulating layer 102 protects the bottom of the substrate 101. Insulating layers 102 and 103 are the etch mask to form a cavity 104 in FIG. 1B. The cavity 104 may be fabricated by standard semiconductor processes, like wet etch tetramethylammonium hydroxide (TMAH), potassium hydroxide (KOH), etc.

In FIG. 1C, a nanopore 105 is formed through the top insulating layer 103. The nanopore 105 is a hole that is few nanometers (e.g., 2, 3, 4, 5, . . . 8 nm) in diameter, and the nanopore 105 can be fabricated by a reactive ion etch method, transmission electron microscopy (TEM), and/or helium ion microscopy (HIM). The nanopore 105 can have different shapes, such as single conical shape, a double conical shape, and/or cylindrical shape. Also, the nanopore 105 may be a nanochannel in some implementations.

FIGS. 2A, 2B, 2C, 2D, and 2E (generally referred to as FIG. 2) illustrate a system 200 incorporating the membrane 100 (i.e., nanodevice) according to an embodiment. FIG. 2 illustrates a cross-sectional view of the system 200.

Figure 2A:
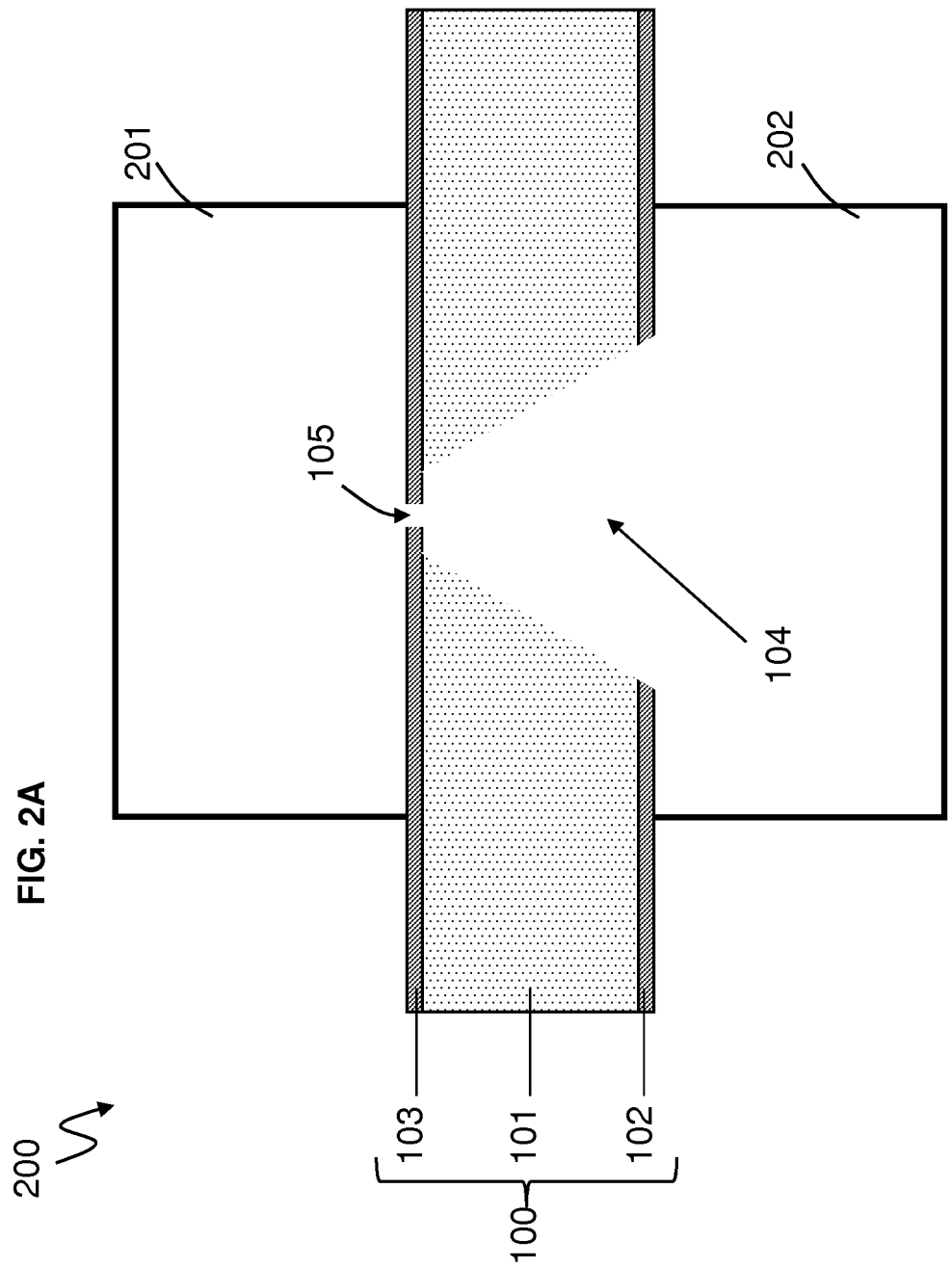
FIG. 2A illustrates a cross-sectional view of a fluidic chamber with a top fluidic reservoir and a bottom fluidic reservoir according to an embodiment.

FIG. 2A shows a fluidic chamber with a top fluidic reservoir 201 and a bottom fluidic reservoir 202. The membrane 200 is sealed to and separates the top and bottom fluidic reservoirs 201 and 202. Although top and bottom fluidic reservoirs are discussed, it is contemplated that the fluidic chamber may be left and right sides.

The top and bottom fluidic reservoirs 201 and 202 may be made of any electrically insulating materials, such as Teflon®, acrylic, and so forth. The top reservoir 201 and bottom reservoir 202 will be filled with a conductive fluid 250.

Figure 2B:
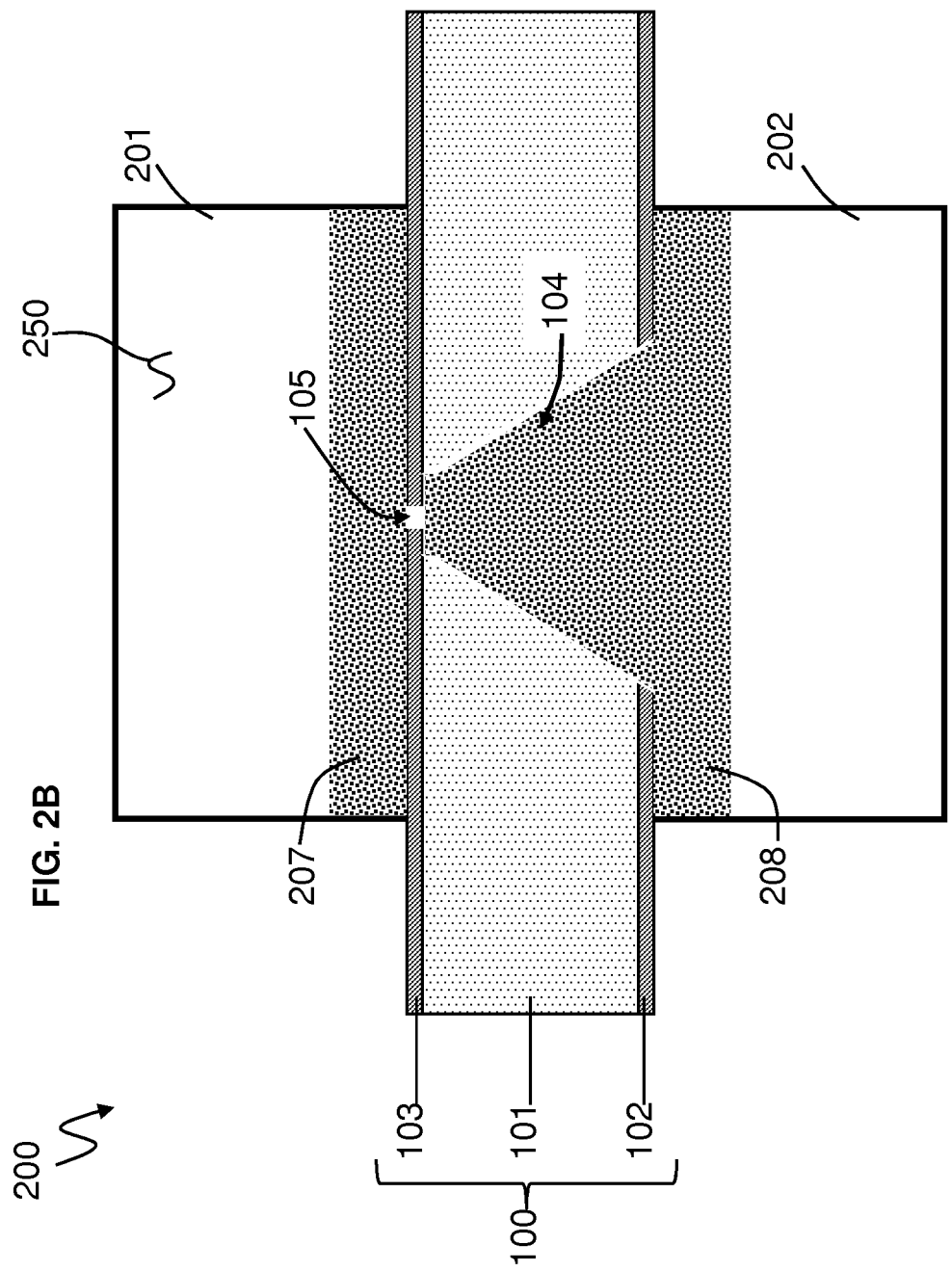
FIG. 2B illustrates agarose gel formed on both sides of the nanopore according to an embodiment.

FIG. 2B shows agarose gel 207 and 208 formed on both sides of the nanopore 105. The agarose gel 207 is formed on the top side of the nanopore 105, and the agarose gel 208 is formed on the bottom side of the nanopore 105. For example, the agarose gel 207 may be poured onto the top side of the insulating layer 103 through the top fluidic chamber 201, such that the agarose gel 207 forms on the insulating layer 103 to a desired thickness. An example thickness of the agarose gel 207 may be 1 to a few (2-9) millimeters (or even centimeters thick).

The agarose gel 208 may be poured onto the bottom side (backside) of the insulating layer 103 through the bottom fluidic chamber 202, such that the agarose gel 208 forms on the backside of the insulating layer 103 to a desired thickness. An example thickness of the agarose gel 208 may be 5 millimeters. Note that the agarose gel is too thick to flow into the narrow diameter of the nanopore 105.

Figure 2C:
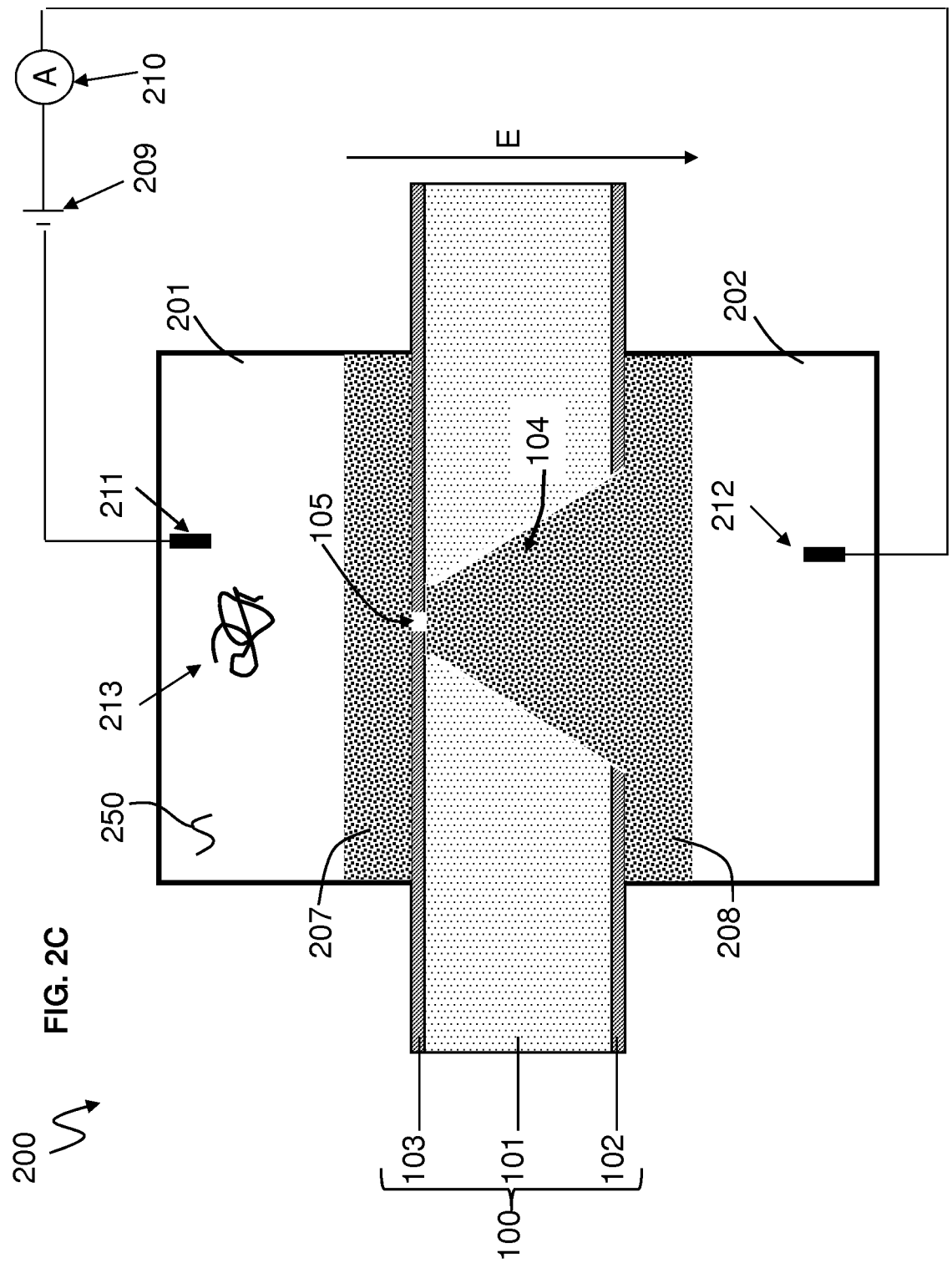
FIG. 2C illustrates that the polyelectrolyte is injected into the top fluidic reservoir as a coil according to an embodiment.

The conductive fluid 250 also fills the top and bottom fluidic chambers 201 and 203. FIG. 2C illustrates that the polyelectrolyte such as a DNA molecule 213 is injected into the top fluidic reservoir 201. FIG. 2C shows a voltage source 209 and an ammeter 210 (ampere meter). The ammeter 210 monitors the current change of the nanopore 105 when voltage of the voltage source 209 is applied. Electrodes 211 and 212 are respectively placed in the conductive fluid 250 of the top and bottom fluidic chambers 201 and 202. The electrodes 211 and 212 may be made of Ag or AgCl. The DNA molecule 213 is pulled through nanopore 105 by the uniform electrical field E (shown by the downward pointing arrow that is actually through the membrane 100 and agarose gels 207, 208 but shown outside so as not to obscure the figures) between electrodes 211 and 212 when voltage is applied by the voltage source 209. Note that the DNA molecule 213 is in a coil (i.e., a ball) before the DNA molecule 213 enters the nanopore 105. A large DNA molecule 213 may have a coil (i.e., coil space) of $1\times10^{-6}$ meters (microns, micrometers, and/or μm) in diameter. While coiled, the DNA molecule 213 has a large entropic barrier to entering the nanopore 105.

However, the agarose gel 207 provides millimeter-scale nanoconfinement to the DNA molecule 213 and prestretches (i.e., uncoils) the DNA molecule 213 before the DNA molecule 213 enters the nanopore 105, which greatly lowers the entropic barrier. The voltage of the voltage source 209 generates the electric field (E) that drives the DNA molecule 213 into the agarose gel 207 and eventually into (and through) the nanopore 105. Yet, before the DNA molecule 213 reaches the entry of the nanopore 105, the DNA molecule 213 is uncoiled as the DNA molecule 213 passes through the agarose gel 207 as shown in FIG. 2D. FIG. 2D shows that the DNA molecule 213 is linearized before the DNA molecule 213 enters into the nanopore 105. The DNA molecule 213 keeps the linearized status (i.e., uncoiled) when the DNA molecule 213 stays inside the agarose gel 207 and/or agarose gel 208 as shown in FIGS. 2D and 2E. FIG. 2E shows the full length of the linearized DNA molecule 213 within the agarose gel 207 and 208 and through the nanopore 105.

According to an embodiment, FIG. 3 illustrates multilayers of agarose gels 207, 208, 301 and 302 (e.g., with different concentrations). The agarose gels 301 and 302 have different pore sizes as compared to agarose gels 207 and 208. The agarose gels 207 and 208 may have the same concentration of agarose material.

The agarose gel has different porous structures at different concentrations of agarose, and thus provides easy tuning of the polyelectrolyte confinement and electric field distribution via the agarose gels 207, 208, 301, and 302. The less the concentration of agarose, the larger the porous structures within the agarose gel. The higher the concentration of agarose, the smaller the porous structure within the agarose gel.

Assume that the agarose gels 207 and 208 have the same internal porous structure with pores that may be (about) 100 nanometers (nm) in diameter (and/or smaller), which is based on the concentration of agarose material in the agarose gels 207 and 208. Assume that the agarose gel 301 has a concentration higher than concentration of the agarose gels 207 and 208, and that the agarose gel 301 has an internal porous structure with pores that may be (about) 250 nm and/or more. Also, assume that the agarose gel 302 has a concentration higher than the concentration of the agarose gel 301, and that the agarose gel 302 has an internal porous structure with pores that may be (about) 350 nm and/or more. By having the varied concentrations of agarose from lowest to highest respectively for the agarose gels 207 to 301 to 302, an agarose gel gradient 350 is created as shown in FIG. 3.

If there is a very large DNA molecule 213 with a 2 μm coil diameter and/or greater (coil space) being driven by the electric field toward the nanopore 105, this large DNA molecule 213 may hit (against) the agarose get 207 but not uncoil when the agarose gel 207 has pores of 100 nm (and/or smaller) in diameter. To ensure that the large DNA molecule 213 (with the 2 μm coil diameter) uncoils, the agarose gel gradient 350 is used. By applying the agarose gel gradient 350, the large DNA molecule 213 first reaches the agarose gel 302 (with the lowest concentration of agarose, e.g., (about) 0.5% of agarose material) having pores 350 nm and/or more in diameter in order to begin uncoiling the DNA molecule 213. These large pores (350 nm and/or more) in the agarose gel 302 start the linearization/stretching of the coiled DNA molecule 213.

Next, the DNA molecule 213 (that has been partially uncoiled) is driven by the electric field (E) to reach the agarose gel 301 (with the middle concentration of agarose, e.g., (about) 0.9% of agarose material) having pores 250 nm and/or more in diameter in order to further uncoil the DNA molecule 213. These medium sized pores (250 nm and/or more) in the agarose gel 301 further linearize and stretch the DNA molecule 213.

Last, the DNA molecule 213 (that has been further uncoiled) is driven by the electric field to reach the agarose gel 207 (with the highest concentration of agarose, e.g., (about) 1.5% of agarose material) having pores (about) 100 nm (and/or smaller) in diameter in order to completely uncoil the DNA molecule 213. These small pores (100 nm and/or less) in the agarose gel 207 linearize and stretch the DNA molecule 213 to fit into the nanopore 105 completely uncoiled.

Although three grades of agarose gel concentrations and internal pore sizes (from largest to smallest) are discussed, some implementations may have more than three grades in the agarose gel gradient 350 in order to begin with even larger internal pores (e.g., 500 nm (and/or more) in diameter) and end with even smaller internal pores (e.g., about 50-75 nm in diameter).

As understood by one skilled in the art, different concentrations of agarose are formed by mixing more or less water to the agarose material. Agarose is a polysaccharide polymer material. Agarose is available as a white powder which dissolves in near-boiling water, and forms a gel when it cools. Agarose gels and melts at different temperatures, and the gelling and melting temperatures vary as understood by one skilled in the art.

Figure 4:
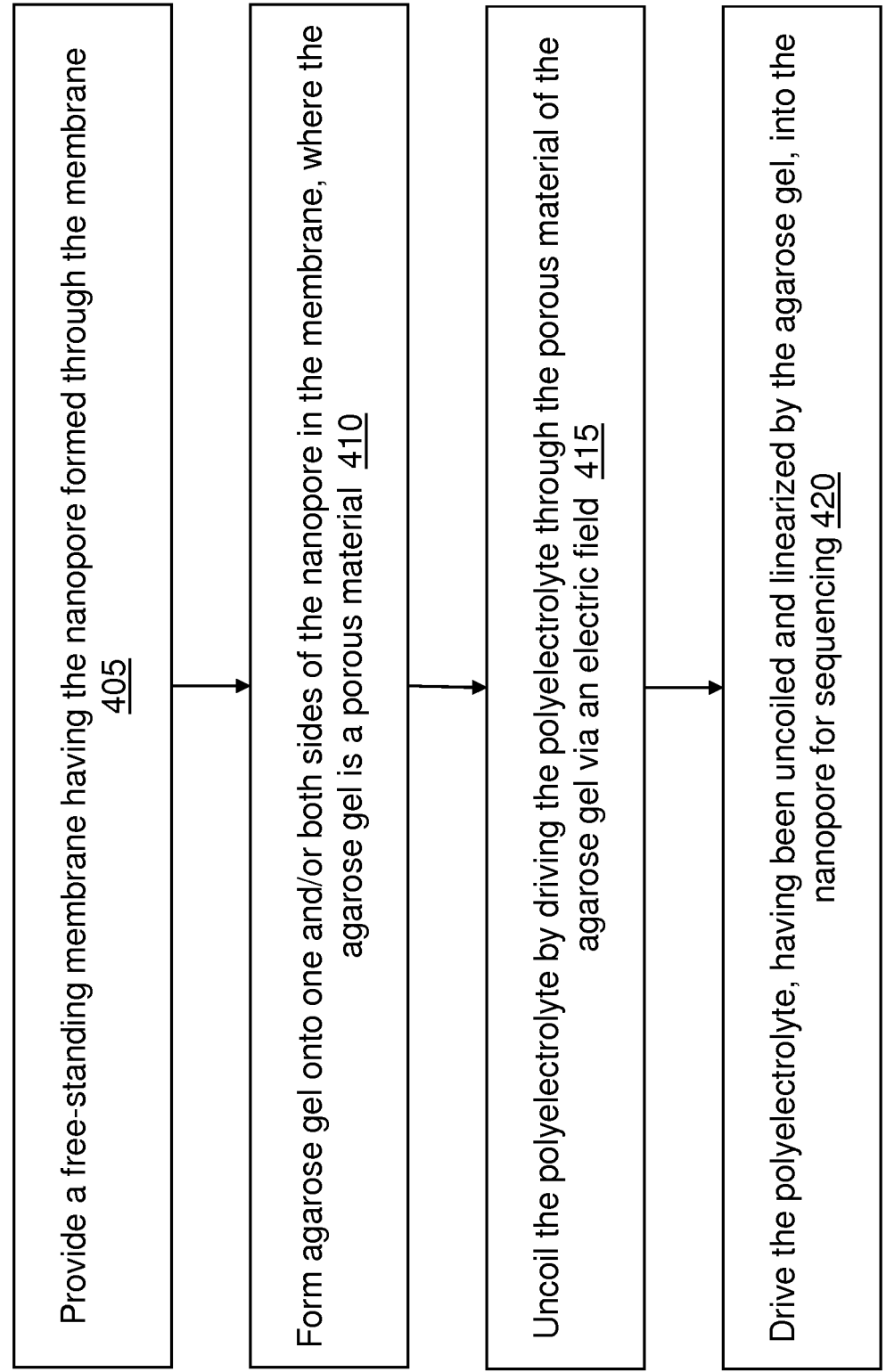
FIG. 4 illustrates a method for reducing entropy of a polyelectrolyte before the polyelectrolyte moves through the nanopore according to an embodiment.

FIG. 4 illustrates a method 400 for reducing entropy of a polyelectrolyte (e.g., molecule 213) before the polyelectrolyte moves through the nanopore 105 according to an embodiment. Reference can be made to FIGS. 1, 2, and 3, along with FIG. 5 discussed below.

The free-standing membrane 100 is provided with the nanopore 105 formed through the membrane 100 at block 405. FIG. 1 illustrates shows how to fabricate a single nanopore 105 but it is understood that an array of nanopores and nanochannels may be formed in the membrane 100.

At block 410, the agarose gels 207 and 208 are formed (poured) onto either or both sides of the nanopore 105 in the membrane 100, and the agarose gel 207 and 208 (301, 302) is a porous material.

At block 415, the polyelectrolyte (molecule 213) is uncoiled by driving the polyelectrolyte through the porous material of the agarose gel 207 (301, 302) via an electric field generated by the voltage of the voltage source 209.

The electric field drives polyelectrolyte (molecule 213), having been uncoiled and linearized by the agarose gel, into the nanopore 105 for sequencing. For example, the ionic current can be measured by the ammeter 210 as each base of the DNA molecule 213 passes through the nanopore 105, which causes a change in the ionic current that corresponds to the identification of the base.

The polyelectrolyte (i.e., molecule 213) is sustained/maintained in an uncoiled and linearized state (i.e., straight) by driving the polyelectrolyte into the agarose gel 208 on the backside of the membrane 100. If the agarose gel 208 were not present on the backside of the membrane 100, the molecule 213 would recoil after exiting the nanopore 105 and/or the agarose gel 207 (on the top side), and the molecule 213 may begin to recoil (into the coil ball, e.g., shown FIG. 2C) before exiting the nanopore 105.

The agarose gel is formed onto both sides of the nanopore 105 in the membrane 100 by applying the agarose gels 207 and 208 respective to a top side and backside of the membrane 100 having the nanopore 105.

The porous material of the agarose gels 207, 208, 301, and 302 have pores of different sizes. The agarose gel may be formed to have different concentrations according to a length of the polyelectrolyte (molecule 213) that is going to be sequence in the nanopore 105. A shorter length resulting in a smaller coil space may only need one concentration of agarose gel 207, while a longer length resulting in a large coil space needs multiple concentrations of agarose gels 207, 301, and 302. Based on the length of the polyelectrolyte having a coil diameter equal to or greater than a predetermined diameter (e.g., $1\times10^{-6}$ m in diameter when the long polyelectrolyte is coiled into a ball), the agarose gel gradient 350 is deposited/formed in order to have a highest concentration of agarose material (e.g., agarose gel 207) closest to nanopore while depositing the agarose gel (e.g., agarose gel 302) with a least concentration of the agarose material farthest from the nanopore 105. The middle concentration of agarose material (agarose gel 301) is in between. For example, the agarose gel is provided onto the top side of the membrane 100 with a gradient (such as agarose gel gradient 350), such that the gradient of agarose gel has largest pores (e.g., in agarose gel 302) farthest from the nanopore 105 and smallest pores (e.g., in agarose gel 207) closest to the nanopore 105.

The agarose gels 207, 302, and 302 of different concentrations correspond to the different internal pore sizes, which are stacked as shown in FIG. 3. The respective pore sizes vary from relatively large at the top of the stack (gradient) to relatively small at the bottom of the stack near the nanopore entrance in order to allow for faster accumulation of the polyelectrolyte near the nanopore entrance as compared to not having the agarose gel with the different concentrations corresponding to the different pore sizes in a stack. The pore sizes that are relatively large may vary/range anywhere from a few microns (such as 1, 2, 3, 4, 5, ... 7 μm) to sub-100-nanometers (such as 60-90 nm) in diameters. The pore sizes that are relatively small correspond to a few tens of nanometers (such as 1, 2, 3, 5, 10, 20, 30 ... 40 nm) in diameter.

The agarose gel 207 (301, 302) has a different thickness on the top side of the nanopore as compared to the thickness of the agarose gel 208 on the backside of the nanopore 105. In one implementation, the agarose gel 207 (301, 302) has the same thickness or approximately the same thickness on both the top side and backside (agarose gel 208) of the nanopore 105. When the agarose gel (e.g., agarose gel 207) is placed on one side of the nanopore 105 in the top fluidic reservoir 201, the polyelectrolyte is put on same side of the nanopore 105 as the agarose gel 207 in the top fluidic reservoir 201. Agarose gel 208 might not be placed on the backside.

The polyelectrolyte includes single-stranded DNA and double-stranded DNA. Also, the polyelectrolyte includes RNA, peptides, and other charged linear polymers.

Figure 5:
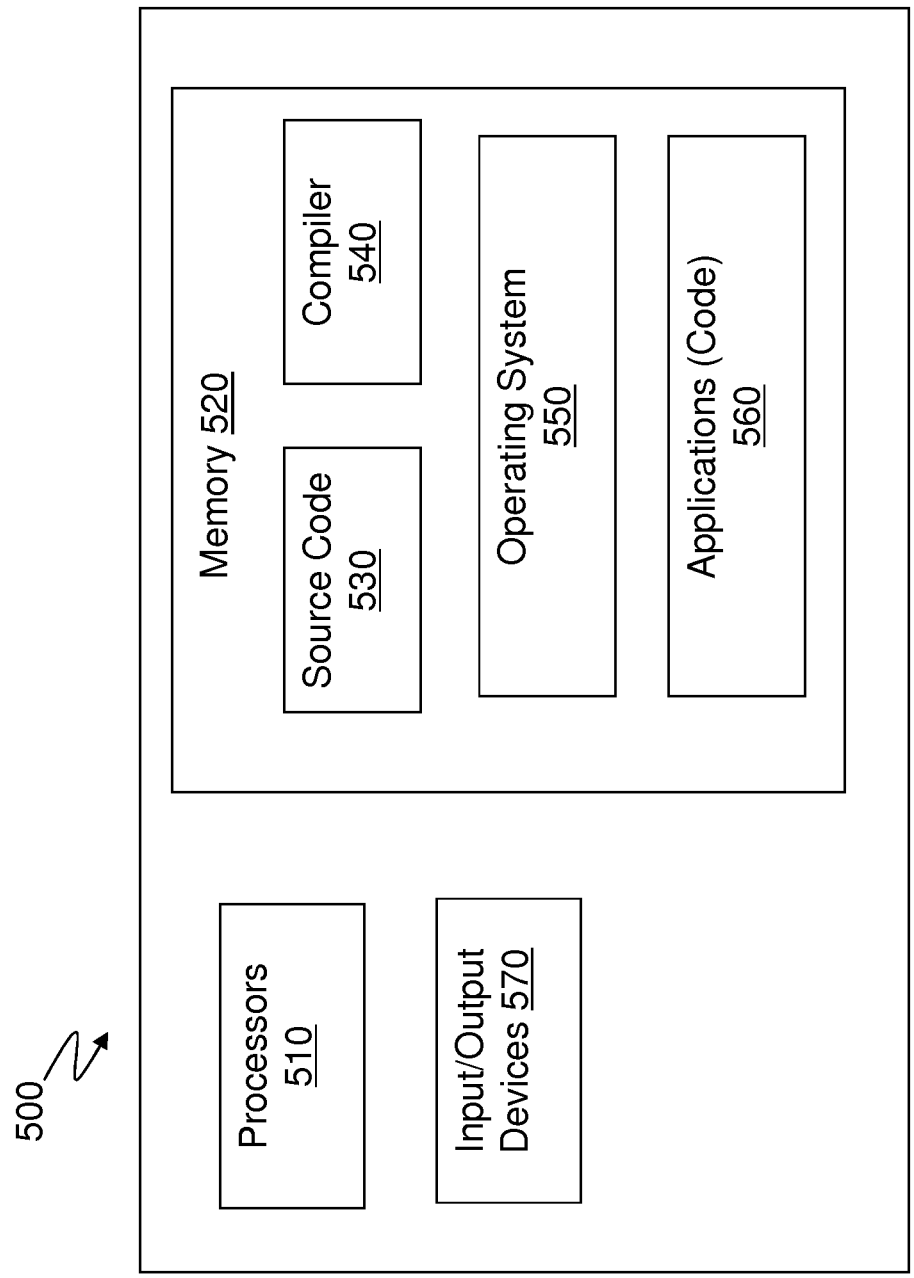
FIG. 5 is a block diagram that illustrates an example of a computer (computer test setup) having capabilities, which may be included in and/or combined with embodiments.

FIG. 5 illustrates an example of a computer 500 (e.g., as part of the computer test setup for testing and analysis) which may implement, control, and/or regulate the voltage of the voltage source 209, and measurements of the ammeter 210 and as discussed herein.

Various methods, procedures, modules, flow diagrams, tools, applications, circuits, elements, and techniques discussed herein may also incorporate and/or utilize the capabilities of the computer 500. Moreover, capabilities of the computer 500 may be utilized to implement features of exemplary embodiments discussed herein. One or more of the capabilities of the computer 500 may be utilized to implement, to connect to, and/or to support any element discussed herein (as understood by one skilled in the art) in FIGS. 1-4. For example, the computer 500 which may be any type of computing device and/or test equipment (including ammeters, voltage sources, connectors, etc.). Input/output device 570 (having proper software and hardware) of computer 500 may include and/or be coupled to the nanodevices and structures discussed herein via cables, plugs, wires, electrodes, patch clamps, etc. Also, the communication interface of the input/output devices 570 comprises hardware and software for communicating with, operatively connecting to, reading, and/or controlling voltage sources, ammeters, and current traces (e.g., magnitude and time duration of current), etc., as discussed herein. The user interfaces of the input/output device 570 may include, e.g., a track ball, mouse, pointing device, keyboard, touch screen, etc., for interacting with the computer 500, such as inputting information, making selections, independently controlling different voltages sources, and/or displaying, viewing and recording current traces for each base, molecule, biomolecules, etc.

Generally, in terms of hardware architecture, the computer 500 may include one or more processors 510, computer readable storage memory 520, and one or more input and/or output (I/O) devices 570 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 510 is a hardware device for executing software that can be stored in the memory 520. The processor 510 can be virtually any custom made or commercially available processor, a central processing unit (CPU), a data signal processor (DSP), or an auxiliary processor among several processors associated with the computer 500, and the processor 510 may be a semiconductor based microprocessor (in the form of a microchip) or a macroprocessor.

The computer readable memory 520 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 520 may incorporate electronic, magnetic, optical, and/or other types of storage media. Note that the memory 520 can have a distributed architecture, where various components are situated remote from one another, but can be accessed by the processor 510.

The software in the computer readable memory 520 may include one or more separate programs, each of which comprises an ordered listing of executable instructions for implementing logical functions. The software in the memory 520 includes a suitable operating system (O/S) 550, compiler 540, source code 530, and one or more applications 560 of the exemplary embodiments. As illustrated, the application 560 comprises numerous functional components for implementing the features, processes, methods, functions, and operations of the exemplary embodiments.

The operating system 550 may control the execution of other computer programs, and provides scheduling, input-output control, file and data management, memory management, and communication control and related services.

The application 560 may be a source program, executable program (object code), script, or any other entity comprising a set of instructions to be performed. When a source program, then the program is usually translated via a compiler (such as the compiler 540), assembler, interpreter, or the like, which may or may not be included within the memory 520, so as to operate properly in connection with the O/S 550. Furthermore, the application 560 can be written as (a) an object oriented programming language, which has classes of data and methods, or (b) a procedure programming language, which has routines, subroutines, and/or functions.

The I/O devices 570 may include input devices (or peripherals) such as, for example but not limited to, a mouse, keyboard, scanner, microphone, camera, etc. Furthermore, the I/O devices 570 may also include output devices (or peripherals), for example but not limited to, a printer, display, etc. Finally, the I/O devices 570 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 570 also include components for communicating over various networks, such as the Internet or an intranet. The I/O devices 570 may be connected to and/or communicate with the processor 510 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 560 is implemented in hardware, the application 560 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A system for reducing entropy of a polyelectrolyte before the polyelectrolyte moves through a nanopore, the system comprising:
   a free-standing membrane having the nanopore formed through the membrane, the membrane including a silicon substrate, an insulating layer, and another insulating layer, wherein the insulating layer is directly on a top surface of the silicon substrate, wherein the another insulating layer is directly on a bottom surface of the silicon substrate, such that the insulating layer and the another insulating layer are not in contact with each other while both the insulating layer and the another insulating layer are in direct contact with opposite surfaces of the silicon substrate, wherein the nanopore is only formed in the insulating layer and has a uniform diameter in the insulating layer such that no nanopore is present in the silicon substrate and the another insulating layer;
   a cavity comprising a narrow end and a wide end formed in the silicon substrate, the narrow end being adjacent to the insulating layer at the nanopore, the narrow end being larger than the nanopore;
   a top fluidic reservoir on one side of the membrane and a bottom fluidic reservoir on an opposing side of the membrane, wherein one surface of the insulating layer is positioned directly on the silicon substrate and an opposite surface of the insulating layer is directly exposed to the top fluidic reservoir such that no layer is positioned on the opposite surface of the insulating layer, wherein one surface of the another insulating layer is positioned directly on the silicon substrate and an opposite surface of the another insulating layer is directly exposed to the bottom fluidic reservoir such that no layer is positioned on the opposite surface of the another insulating layer;
a first agarose gel formed onto both sides of the nanopore in the membrane, wherein the first agarose gel is formed directly on both the insulating layer and the another insulating layer, the first agarose gel being formed directly on sidewalls of the silicon substrate which form the cavity such that the first agarose gel fills an entirety of the cavity, wherein a top surface of a portion of the insulating layer extends beyond edges of the top fluidic reservoir such that the portion of the top surface of the insulating layer is exposed and free of the first agarose gel while the top surface of another portion of the insulating layer is within the top fluidic reservoir and is in direct contact with the first agarose gel;
a second agarose gel formed directly on the first agarose gel in the top fluidic reservoir, such that the second agarose gel and the insulating layer sandwich a portion of the first agarose gel in the top fluidic reservoir;
a third agarose gel formed directly on top of the second agarose gel in the top fluidic reservoir, the bottom fluidic reservoir being free from the second and third agarose gels; and
an electric field generated by a voltage source that drives the polyelectrolyte through the porous material of the agarose gel to uncoil the polyelectrolyte, wherein driving the polyelectrolyte, having been uncoiled and linearized by the agarose gel, into the nanopore is for sequencing.

2. The system of claim 1, wherein the polyelectrolyte is sustained in an uncoiled and linearized state by driving the polyelectrolyte into the first agarose gel on a backside of the membrane.

3. The system of claim 1, wherein the first agarose gel is formed onto both sides of the nanopore in the membrane by applying the first agarose gel to a top side and backside of the membrane having the nanopore.

4. The system of claim 1, wherein a porous material of the first, second, and third agarose gels have pores of different sizes.

5. The system of claim 1, wherein the first, second, and third agarose gels are formed to have different concentrations according to a length of the polyelectrolyte.

6. The system of claim 1, wherein a wide end of the cavity is formed through the another insulating layer.

7. The system of claim 1, wherein the first agarose gel is formed in the cavity.

8. The system of claim 1, wherein no intervening layer is present between the narrow end of the cavity adjacent to the insulating layer at the nanopore.

9. The system of claim 1, wherein the nanopore is cylindrical.

10. The system of claim 1, wherein the nanopore and the cavity are formed in two separate layers.

11. The system of claim 1, wherein the free-standing membrane comprises only 3 layers.

12. The system of claim 1, wherein no layer of the free-standing membrane is conductive.

* * * * *